United States Patent [19]
Moriya et al.

[11] Patent Number: 5,385,891
[45] Date of Patent: Jan. 31, 1995

[54] POLYSULFATE OF β-CYCLODEXTRIN DERIVATIVE AND PROCESS FOR PREPARING THE SAME

[75] Inventors: Tamon Moriya, Takatsuki; Hironori Kurita, Warabi; Toru Otake, Kashiba; Haruyo Mori, Nara; Motoko Morimoto, Hirakata, all of Japan

[73] Assignee: Tanabe Seiyaku Co., Ltd., Osaka, Japan

[21] Appl. No.: 928,319

[22] Filed: Aug. 12, 1992

[30] Foreign Application Priority Data

Aug. 29, 1991 [JP] Japan .................. 3-299983
Feb. 20, 1992 [JP] Japan .................. 4-085119

[51] Int. Cl.⁶ ............................ C08B 37/00
[52] U.S. Cl. ...................... 514/58; 536/103; 536/112
[58] Field of Search ............ 514/58; 536/103, 112

[56] References Cited

U.S. PATENT DOCUMENTS

| | | | |
|---|---|---|---|
| 3,974,274 | 8/1976 | Kurita et al. | 536/103 |
| 4,020,160 | 4/1977 | Bernstein et al. | 536/103 |
| 4,066,829 | 1/1978 | Nair et al. | 536/103 |
| 4,258,180 | 3/1981 | Lewis et al. | 536/122 |
| 4,783,446 | 11/1988 | Neushul | 514/54 |
| 4,840,941 | 6/1989 | Ueno et al. | 514/59 |
| 5,134,127 | 7/1992 | Stella et al. | 514/58 |

FOREIGN PATENT DOCUMENTS

| | | |
|---|---|---|
| 0119453 | 9/1984 | European Pat. Off. . |
| 0447171 | 9/1991 | European Pat. Off. . |
| 0485614 | 5/1992 | European Pat. Off. . |
| 63-45223 | 2/1988 | Japan . |
| 64-25724 | 1/1989 | Japan . |
| 2-304025 | 12/1990 | Japan . |
| WO9000596 | 1/1990 | WIPO . |

OTHER PUBLICATIONS

Hartman, et al., Aids Research and Human Retroviruses, vol. 6, No. 6, pp. 805–812 (1990).
Igakunoayumi, vol. 142, No. 9, pp. 619–622 (1987).
C. P. Bianchi, Chemical Abstracts, vol. 113, No. 21, Abstract No. 184254s (1990).
Croft et al., "Synthesis of Chemically Modified Cyclodextrins", Tetrahedron Report Number 147, *Tetrahedron*, vol. 39, No. 9, pp. 1417 to 1474, 19983 (Pergamon Press Ltd.-Oxford, G.B.).

*Primary Examiner*—Ronald W. Griffin
*Attorney, Agent, or Firm*—Birch, Stewart, Kolasch & Birch

[57] ABSTRACT

Disclosed is a polysulfate of a β-cyclodextrin in which at least one of 7 D-glucose units constituting the β-cyclodextrin is a unit represented by the formula (I-a):

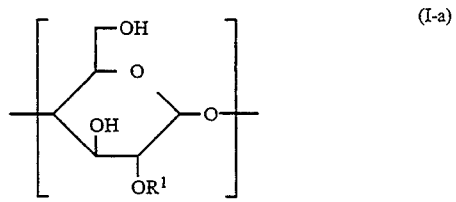

wherein $R^1$ is an alkyl group having 1 to 8 carbon atoms, a lower alkyl group having a substituent(s) or a lower alkenyl group, or a salt thereof, which has excellent antiretrovirus activity and is useful as an antiretrovirus agent.

7 Claims, No Drawings

POLYSULFATE OF β-CYCLODEXTRIN DERIVATIVE AND PROCESS FOR PREPARING THE SAME

BACKGROUND OF THE INVENTION

This invention relates to a novel polysulfate of a β-cyclodextrin derivative having antiretrovirus activity and processes for preparing the same.

AIDS (acquired immunodeficiency syndrome) is a lethal or extremely malignant disease which is caused by infection of human immunodeficiency virus (HIV) which is a kind of retrovirus. The prevention and destruction thereof are now a most serious problem to be overcome by human beings, with world-wide scale.

As compounds having antiretrovirus activity, there have been known, for example, azidothimidine (IGAKUNOAYUMI (Walking of Medicine), Vol. 142, No. 9, pp. 619 to 622 (1987)), sulfated polysaccharides (Japanese Provisional Patent Publications No. 45223/1988 and No. 25724/1989), and the like.

However, it has not yet fully been made clear or confirmed whether or not conventionally known chemicals having antiretrovirus activity are effective for and safe for use in the therapy of AIDS.

SUMMARY OF THE INVENTION

An object of the present invention is to provide a novel pharmaceutical compound having excellent antiretrovirus activity, particularly excellent proliferation inhibitory activity against HIV.

The present invention relates to a polysulfate of a lipophilic group-modified β-cyclodextrin. More particularly, it relates to a polysulfate of a β-cyclodextrin (hereinafter referred to as "polysulfate compound") in which at least one of 7 D-glucose units constituting the β-cyclodextrin is a unit represented by the formula (I-a):

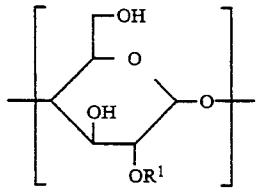

wherein $R^1$ is an alkyl group having 1 to 8 carbon atoms, a lower alkyl group having a substituent(s) or a lower alkenyl group, or a salt thereof.

A process for preparing the above-defined polysulfate compound of the present invention comprises reacting a β-cyclodextrin derivative in which at least one of 7 D-glucose units constituting the β-cyclodextrin is a unit represented by the formula (I-a), with a sulfonating agent, and then converting the product into a salt, if desired.

DESCRIPTION OF THE PREFERRED EMBODIMENTS

In the following, the present invention is explained in detail.

The polysulfate compound of the present invention may be represented more specifically as follows:

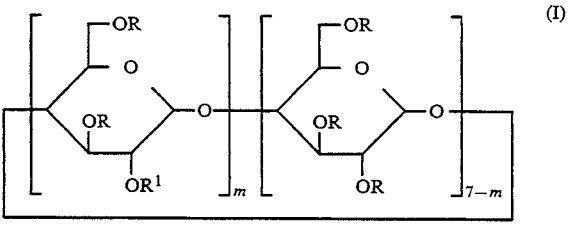

wherein m represents an integer of 1 to 7, at least one of Rs represents a —SO$_3$H group and the other Rs represent hydrogen atom, and $R^1$ has the same meaning as defined above.

In the above formula (I), the 7 constitutional units are forming a cyclic ring in an arbitrary order through linkage between the 1-position and the 4-position.

As a specific example of the polysulfate compound of the present invention, there may be mentioned compounds of the formula (I) in which $R^1$ is an alkyl group having 1 to 8 carbon atoms, a phenyl-substituted lower alkyl group (e.g. benzyl group and phenethyl group), a halogenophenyl-substituted lower alkyl group (e.g. chlorobenzyl group and fluorobenzyl group), a lower alkylphenyl-substituted lower alkyl group (e.g. methylbenzyl group and ethylbenzyl group) or a lower alkenyl group (e.g. allyl group and pentenyl group).

Of the polysulfate compounds (I) of the present invention, preferred is a compound in which $R^1$ is a phenyl-substituted lower alkyl group or a halogenophenyl-substituted lower alkyl group, and more preferred is a compound in which $R^1$ is benzyl group, fluorobenzyl group or chlorobenzyl group.

The polysulfate compound (I) of the present invention has preferably 8 to 20, particularly preferably 9 to 18 sulfate groups.

In the present invention, the lower alkyl group includes those having 1 to 6, particularly 1 to 4 carbon atoms, and the lower alkenyl group includes those having 2 to 6 carbon atoms.

The polysulfate compound (I) of the present invention can be prepared by reacting a β-cyclodextrin derivative in which at least one of 7 D-glucose units constituting the β-cyclodextrin is a unit represented by the formula (I-a), with a sulfonating agent.

The reaction may be illustrated as follows:

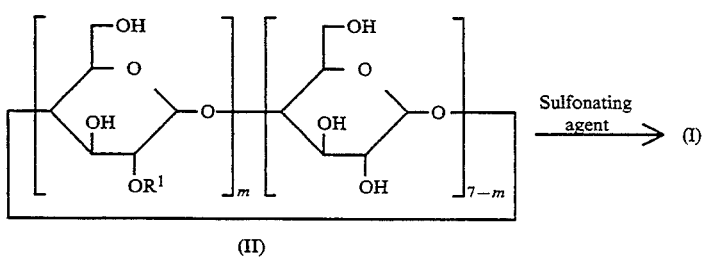

(II)

wherein the symbols each have the same meanings as defined above.

Of the desired compounds (I) of the present invention, a compound in which the 6-positions of the 7 D-glucose units are all free hydroxy groups can be prepared by reacting a β-cyclodextrin derivative in which at least one of 7 D-glucose units constituting the β-cyclodextrin is a unit represented by the formula (I-b):

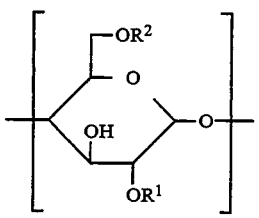

(I-b)

wherein $R^2$ represents a protective group for hydroxy group, and $R^1$ has the same meaning as defined above, and the remaining unit(s) is/are a unit(s) represented by the formula (I-c):

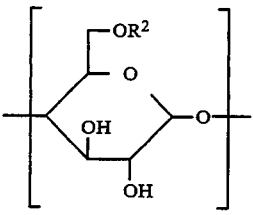

(I-c)

wherein the symbol has the same meaning as defined above, with a sulfonating agent, and then removing a protective group for hydroxy group.

The reaction may be illustrated as follows:

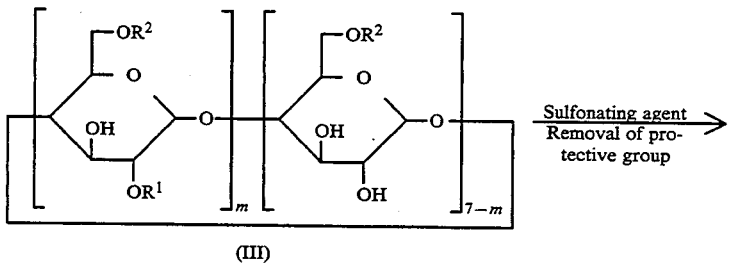

(III)

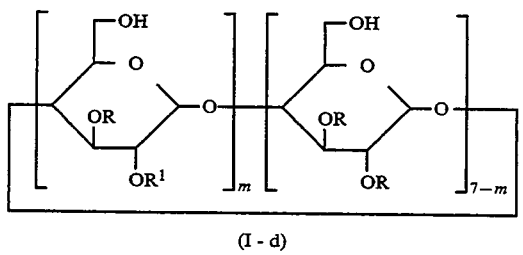

(I-d)

wherein the symbols each have the same meanings as defined above.

In the above Compound (III), the protective group ($R^2$) for hydroxy group is not particularly limited so long as it is generally used in this field, and there may be used, for example, a lower alkyl group-substituted silyl group such as t-butyldimethylsilyl group, trimethylsilyl group and triisopropylsilyl group; an acyl group such as acetyl group, benzoyl group, ethoxycarbonyl group and pivaloyl group; or trityl group.

The reaction of Compound (II) or (III) with the sulfonating agent may be carried out in a suitable solvent. As the sulfonating agent, there may be suitably used, for example, a sulfur trioxide complex (e.g. sulfur trioxide-pyridine complex, sulfur trioxide-trialkylamine complex, sulfur trioxide-dioxane complex and sulfur trioxide-dimethylformamide complex), anhydrous sulfuric acid, concentrated sulfuric acid and chlorosulfonic acid.

The amount of the sulfonating agent to be used may preferably be in excess of the amount of Compound (II) or (III). For example, in cases where sulfur trioxide-pyridine complex or sulfur trioxide-trialkylamine complex is used as the sulfonating agent, the amount thereof to be used may be preferably 1 to 10 equivalents, particularly preferably about 2 to 5 equivalents relative to the amount of hydroxy group of Compound (II) or (III).

As the solvent for reaction, there may be preferably used, for the example, a tertiary amine (e.g. pyridine, picoline, lutidine and N,N-dimethylaniline), N,N-dimethylformamide, formamide, hexamethylenephosphoryltriamide, chloroform, benzene, toluene, xylene, water, a mixture thereof and liquid sulfur dioxide.

The present reaction can be carried out under cooling to under heating and may be particularly desirably carried out under heating. When sulfur trioxide complex or chlorosulfonic acid is used as sulfonating agent in pyridine, the reaction can be carried out preferably at 30° to 200° C., particularly preferably at 60° to 120° C.

When Compound (III) is reacted with the sulfonating agent, a protective group for the hydroxy group can be removed from the resulting product according to a conventional manner depending on the kind of the protective group. For example, when the protective group is a lower alkyl group-substituted silyl group such as t-butyldimethylsilyl group, the protective group can be removed by treating with a conventional desilylating agent such as an acid, a fluorine compound, a base and an oxidizer in a solvent (water, a lower alkanol such as methanol and ethanol, dioxane, tetrahydrofuran, acetonitrile or a mixture thereof) under cooling to heating. As the acid, there may be mentioned a mineral acid or an organic acid such as hydrochloric acid, hydrofluoric acid, hydrobromic acid, sulfuric acid, acetic acid, trifluoroacetic acid, citric acid and p-toluenesulfonic acid, and as the fluorine compound, there may be mentioned tetrabutylammonium fluoride and cesium fluoride. Further, as the base, there may be mentioned alkali metal hydroxide and alkaline earth metal hydroxide, and as the oxidizer, there may be mentioned bromine and N-bromosuccinimide. When the protective group is acyl group or trityl group, said protective group can be removed by hydrolysis. The hydrolysis can be carried out by, for example, treating with an alkali reagent (e.g. sodium hydroxide and potassium hydroxide) or an acid (e.g. hydrochloric acid and hydrobromic acid) in a suitable solvent (e.g. methanol, ethanol and water) under cooling to heating.

After completion of the sulfonation reaction or the reaction for removing the protective group, the desired product can be isolated and purified according to a conventional manner. For example, the crude product obtained from the reaction mixture is treated with an alkali metal hydroxide, followed by being passed through a column packed with a cross-linked dextran gel to give the desired product as an alkali metal salt.

The starting compounds (II) and (III) to be used in the present invention can be prepared according to, for example, the method described in Carbohydrate Research, Vol. 187, pp. 203 to 221 (1989).

The polysulfate compound of the present invention may be suitably used either in a free form or in the form of a pharmaceutically acceptable salt thereof. As such salts, there may be mentioned, for example, an alkali metal salt such as a sodium salt, a potassium salt and a lithium salt, an alkaline earth metal salt such as a calcium salt, a magnesium salt and a barium salt, and an organic amine salt such as a trimethylamine salt, a triethylamine salt, a pyridine salt, a glycine ethyl ester salt, an ethanolamine salt and a basic amino acid salt.

The polysulfate compound or a salt thereof of the present invention may be administered either orally or parenterally (e.g. intravenous, intramuscular and subcutaneous administrations), and may be used in an ordinary manner, e.g. as an optional pharmaceutical preparation such as a tablet, a granule, a capsule, a powder, an injection preparation, a suppository, a pessary and a cream.

The dosage amount of the compound of the present invention to be administered as an active ingredient is different depending upon the age, body weight, conditions and the kind of symptoms of a patient and may be suitably around 0.1 to 500 mg/kg, particularly preferably around 1.0 to 50 mg/kg.

EXAMPLES

The present invention is described in detail by referring to Examples.

Example 1

To 4.70 g of heptakis(2-O-benzyl)-$\beta$-cyclodextrin was added 230 ml of pyridine, and the mixture was heated to 100° C. Subsequently, 17.8 g of sulfur trioxide-pyridine complex was added thereto, and the mixture was stirred at the same temperature for 8 hours. Pyridine was removed under reduced pressure, and the residue was dissolved in a mixed solution of 20 ml of water and 50 ml of methanol. Then, 700 ml of methanol was further added to the solution, and the mixture was left to stand in a cool place overnight. The supernatant was removed from the solution, and the residue was washed with methanol and then dissolved in 100 ml of water. To the resulting solution was added 2.6 g of sodium hydroxide, and the mixture was stirred at room temperature for 30 minutes. The reaction mixture was evaporated to dryness under reduced pressure, and the residue was treated with methanol to be powdered. The resulting powder was collected by filtration, dried and then dissolved in water. The resulting solution was passed through a column packed with Sephadex G-10 (trade name, manufactured by Pharmacia AB) (eluent-:water). The fractions containing the desired product were collected, treated with activated carbon and filtered by a membrane filter. The filtrate was lyophilized to give 6.91 g of sodium salt of heptakis(2-O-benzyl)-$\beta$-cyclodextrin polysulfate as a colorless powder.

IR$^{KBr}$ $\nu_{max}$ cm$^{-1}$: 3492, 1635, 1500, 1455, 1239, 1165, 1140, 1100, 1055, 993, 940, 808, 745

$^1$H-NMR (D$_2$O) $\delta$: 3.8~4.1 (m, 14H), 4.1~4.3 (m, 7H), 4.27 (brs, 14H), 4.54 (brs, 14H), 4.6~4.9 (m, 7H), 5.21 (d, 7H), 7.1~7.5 (m, 35H)

The number of sulfate groups in the molecule to be calculated from the elementary analysis value: 14

Examples 2 to 12

The corresponding starting compounds were treated in the same manner as in Example 1 to give the compounds as shown in the following Table 1.

TABLE 1

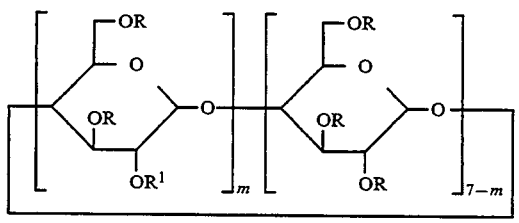

(I)

(provided that 7 constitutional units are forming a cyclic ring in an arbitrary order through linkage between the 1-position and the 4-position)

| Example No. | Compound (I) $R^1$ | m | Number of sulfate groups* | Kind of salt | Physical properties Form | Yield** (%) | IR $\nu$ cm$^{-1}$*** | $^1$H-NMR (D$_2$O) $\delta$ |
|---|---|---|---|---|---|---|---|---|
| 2 | —CH$_2$—C$_6$H$_5$ | 3 | 16 | K | Colorless powder | 62 | 3494, 1639, 1500, 1455, 1240, 1116, 1060, 1035, 1002, 945, 815, 747 | 3.0~6.0(m), 7.0~7.8(m) |
| 3 | —CH$_2$—C$_6$H$_5$ | 2 | 18 | K | Colorless powder | 239 | 3530, 1641, 1240, 1162, 1056, 1035, 1003, 943, 813, 744 | 3.0~5.7(m), 7.1~7.7(m) |
| 4 | —CH$_3$ | 7 | 14 | Na | Colorless powder | 58 | 3500, 1640, 1270, 1220, 1150, 1060, 990, 940, 820, 740 | 3.53(s, 21H), 3.75~3.85(m, 7H), 4.17 (brs, 14H), 4.25~4.50(m, 14H), 4.6~4.9(m, 7H), 5.33 (d, 7H) |
| 5 | —CH$_2$—C$_6$H$_4$—CH$_3$ | 7 | 14 | Na | Colorless powder | 75 | 3500, 1640, 1230, 1160, 1060, 990, 940, 810, 720 | 2.21(s, 21H), 3.97 (brs, 14H), 4.25(br tri, 21H), 4.55 (brs, 7H), 4.6~4.95(m, 14H), 5.22 (d, 7H), 7.1~7.3 (m, 28H) |
| 6 | —CH$_2$—C$_6$H$_4$—F | 7 | 14 | Na | Colorless powder | 51.5 | 3420, 1640, 1600, 1260, 1220, 1160, 1060, 990, 940, 820, 740 | 3.8~4.0(m, 14H), 4.05~4.2(m, 7H), 4.28(brs, 14H), 4.50(brs, 7H), 4.6~4.9(m, 14H), 5.20 (d, 7H), 7.02(tri, 14H), 7.22(tri, 14H) |
| 7 | —CH$_2$—C$_6$H$_4$—Cl | 7 | 14 | Na | Colorless powder | 105 | 3500, 1630, 1240, 1160, 1100, 1060, 990, 950, 820, 780, 720 | 3.8~4.0(m, 14H), 4.1~4.25(m, 14H), 4.34(tri, 7H), 4.50 (brs, 7H), 4.6~4.8 (m, 14H), 5.25(d, 7H), 7.0~7.4(m, 28H) |
| 8 | —CH$_2$CH=CH$_2$ | 7 | 14 | Na | Colorless powder | 129 | 3518, 1644, 1240, 1160, 1110, 1065, 999, 946, 820, 744 | 3.5~5.0(m, 56H), 5.0~5.6(m, 21H), 5.8~6.2(m, 7H) |
| 9 | —CH$_2$CH=CHC$_2$H$_5$ | 7 | 14 | Na | Colorless powder | 127 | 3507, 1641, 1236, 1150, 1106, 1063, 996, 947, 821, 749 | 0.96(t, 21H), 1.9~2.3(m, 14H), 3.7~4.6(m, 49H), 4.6~5.0(m, 7H), 5.30 (d, 7H), 5.4~5.9 (m, 14H) |
| 10 | -n-C$_8$H$_{17}$ | 1 | 17 | Na | Colorless powder | 215 | 3524, 1637, 1240, 1145, 1055, 1040, 1010, 950, 890, 824, 750 | 0.7~1.1(m, 3H), 1.1~1.6(m, 10H), 1.6~1.9(m, 2H), 3.3~5.2(m, 44H), 5.3~5.8(m, 7H) |
| 11 | -n-C$_3$H$_7$ | 7 | 14 | Na | Colorless powder | 159 | 3534, 1643, 1237, 1145, 1105, 1060, 995, 940, 816, 746 | 0.92(t, 21H), 1.4~1.8(m, 14H), 3.4~3.8(m, 14H), 3.8~4.6(m, 35H), 4.7~4.9(m, 7H), 5.30 |

TABLE 1-continued

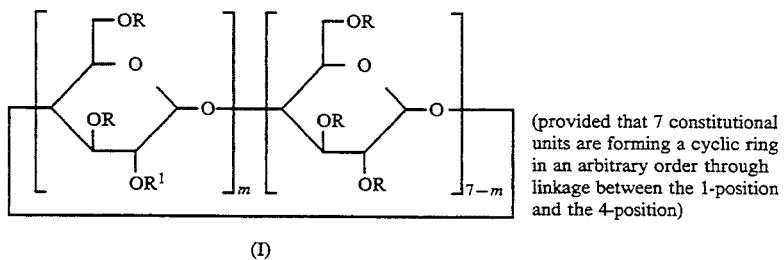

(provided that 7 constitutional units are forming a cyclic ring in an arbitrary order through linkage between the 1-position and the 4-position)

(I)

| Example No. | Compound (I) | | | Physical properties | | | |
|---|---|---|---|---|---|---|---|
| | $R^1$ | Number of sulfate groups* | Kind of salt | Form | Yield** (%) | IR $\nu$ cm$^{-1}$*** | $^1$H-NMR (D$_2$O) $\delta$ |
| 12 | -n-C$_5$H$_{11}$ | 7 | 14 | Na | Colorless powder | 100 | 3496, 1635, 1240, 1145, 1105, 1060, 996, 945, 818, 750 | (d, 7H) 0.8~1.2(m, 21H), 1.2~1.5(m, 28H), 1.5~2.0(m, 14H), 3.5~4.5(m, 49H), 4.6~5.1(m, 7H), 5.27(d, 7H) |

*: The number of sulfate groups in one molecule to be calculated from the elementary analysis value.
**: Yield is shown in terms of % by weight of the desired product relative to the starting compound.
***: KBr was used in Examples 2, 3 and 8 to 12, and Nujol was used in Examples 4 to 7.

Example 13

To 331 mg of tris(2-O-benzyl)-heptakis(6-O-t-butyldimethylsilyl)-β-cyclodextrin was added 30 ml of pyridine, and the mixture was heated to 100° C. Subsequently, 788 mg of sulfur trioxide-pyridine complex was added thereto, and the mixture was stirred at the same temperature for 6 hours. Pyridine was removed under reduced pressure, and the residue was dissolved in a mixed solution of 10 ml of water and 10 ml of methanol. Then, 10 ml of 5% hydrochloric acid was further added to the solution, and the mixture was stirred at room temperature for 30 minutes. To the resulting solution was added 2 g of potassium hydroxide under cooling, and the mixture was stirred at room temperature for 30 minutes. The reaction mixture was evaporated to dryness under reduced pressure, and the residue was dissolved in 20 ml of water and treated with activated carbon. The resulting solution was dialyzed for 2 hours by using a dialysis membrane (a visking seamless cellulose membrane produced by Shiraimatsu Kikai K.K.), further dialyzed for 2 hours after exchange of water and then condensed. The condensate was passed through a column packed with Sephadex G-10 (trade name, manufactured by Pharmacia AB) (eluent:water). The fractions containing the desired product were collected, treated with activated carbon and filtered by a membrane filter. The filtrate was lyophilized to give 230 mg of potassium salt of tris(2-O-benzyl)-β-cyclodextrin polysulfate (provided that hydroxy group at the 6-position was not sulfated) as a colorless powder.

IR$^{KBr}$ $\nu_{max}$ cm$^{-1}$: 1641, 1236, 1138, 1008, 950, 817, 755
$^1$H-NMR (D$_2$O) $\delta$: 3.0~6.0 (m), 6.9~7.9 (m)

The number of sulfate groups in the molecule to be calculated from the elementary analysis value: 9

Example 14

The corresponding starting compound was treated in the same manner as in Example 13 to give potassium salt of bis(2-O-benzyl)-β-cyclodextrin polysulfate (provided that hydroxy group at the 6-position was not sulfated) as a colorless powder.

IR$^{KBr}$ $\nu_{max}$ cm$^{-1}$: 1640, 1246, 1164, 1010, 956, 824, 754
$^1$H-NMR (D$_2$O) $\delta$:3.0~5.6 (m), 6.9~7.7 (m)

The number of sulfate groups in the molecule to be calculated from the elementary analysis value: 10

Reference Example 1

In 150 ml of N,N-dimethylformamide was dissolved 6.2 g of heptakis(6-O-t-butyldimethylsilyl)-β-cyclodextrin, and to the solution were added 3.54 g of barium oxide and 1.83 g of barium hydroxide octahydrate. After 1.14 g of benzyl bromide was added dropwise to the mixture while stirring and under ice cooling, the resulting mixture was stirred at room temperature for 18 hours. The insolubles were removed by filtration, and then 300 ml of ethyl acetate was added to the residue. The mixture was washed successively with diluted hydrochloric acid, water and a saturated saline solution. The mixture was dried over magnesium sulfate and evaporated to dryness under reduced pressure. The residue was separated and purified by silica gel column chromatography (solvent: chloroform:methanol=95:5 to 9:1) to give the following compounds.

Bis(2-O-benzyl)-heptakis(6-O-t-butyldimethylsilyl)-β-cyclodextrin
Yield: 1.2 g
Form: caramel
$^1$H-NMR (CDCl$_3$) $\delta$: 0.00 (s, 42H), 0.84 (s, 63H), 3.1~4.2 (m, 42H), 4.3~5.4 (m, 16H), 5.6~6.5 (m, 7H), 7.0~7.5 (m, 10H)

Tris (2-O-benzyl)-heptakis (6-O-t-butyldimethylsilyl)-β-cyclodextrin
Yield: 1.3 g
Form: caramel
$^1$H-NMR (CDCl$_3$) $\delta$: 0.00 (s, 42H), 0.85 (s, 63H), 3.1~4.2 (m, 42H), 4.4~6.3 (m, 24H), 7.0~7.5 (m, 15H)

Reference Examples 2 to 9

The corresponding starting compounds were treated in the same manner as in Reference example 1 to give the compounds as shown in the following Table 2.

onto column chromatograph packed with 30 ml of a high porous polymer CHP-20P (trade name, produced by MITSUBISHI KASEI CORPORATION). The resulting product was washed successively with 100 ml of water and each 50 ml of 20% methanol and 50%

TABLE 2

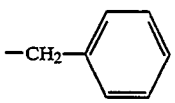

(III)

(provided that 7 constitutional units are forming a cyclic ring in an arbitrary order through linkage between the 1-position and the 4-position, $R^2$ = t-butylmethylsilyl group)

| Reference example No. | Compound (III) R¹ | m | Form | Yield (%) | ¹H-NMR(CDCl₃) δ or m.p. |
|---|---|---|---|---|---|
| 2 | —CH₂—C₆H₅ | 7 | Needle-shaped | 13 | m.p.: 199~201° C. |
| 3 | —CH₃ | 7 | Colorless powder | 82 | m.p.: 215~220° C. |
| 4 | —CH₂—C₆H₄—CH₃ | 7 | Caramel | 11 | −0.03(s, 42H), 0.82(s, 63H), 2.35(s, 21H), 3.2~4.0(m, 42H), 4.6~4.7(m, 7H), 4.73 (brs, 7H), 4.85~4.95(brs, 14H), 7.05~7.25(m, 28H) |
| 5 | —CH₂—C₆H₄—F | 7 | Caramel | 24 | 0.00(s, 42H), 0.84(s, 63H), 3.2~4.0(m, 42H), 4.6~4.8 (m, 14H), 4.8~4.95(m, 14H), 6.9~7.1(m, 14H), 7.2~7.4 (m, 14H) |
| 6 | —CH₂—C₆H₄—Cl | 7 | Colorless powder | 30 | m.p.: 115~120° C. |
| 7 | —CH₂CH=CH₂ | 7 | Colorless powder | 22 | m.p.: 163~166° C. |
| 8 | —CH₂CH=CHC₂H₅ | 7 | Colorless powder | 8 | m.p.: 179~182° C. |
| 9 | -n-C₈H₁₇ | 1 | Colorless powder | 20 | m.p.: 238~240° C. (decomposed) |

Reference Example 10

In 8 ml of tetrahydrofuran was dissolved 635 mg of bis(2-O-benzyl)-heptakis( 6-O-t-butyldimethylsilyl )-β-cyclodextrin. To the resulting mixture was added 2.5 ml of a tetrahydrofuran solution (one mole concentration solution) of n-tetrabutylammonium fluoride, and the mixture was refluxed under heating for 2 hours. Tetrahydrofuran was removed under reduced pressure, and water and ethyl acetate were added to the residue. After the aqueous layer was collected and condensed under reduced pressure, the condensate was applied onto column chromatograph packed with 30 ml of a high porous polymer CHP-20P (trade name, produced by MITSUBISHI KASEI CORPORATION). The resulting product was washed successively with 100 ml of water and each 50 ml of 20% methanol and 50% methanol, and eluted with 70% methanol. The eluate was collected and evaporated to dryness under reduced pressure. The residue was washed with acetone, collected by filtration and dried to give 270 mg of bis(2-O-benzyl)-β-cyclodextrin as a colorless powder.
m.p.: 260°~262° C. (decomposed)

Reference Examples 11 to 19

The corresponding starting compounds were treated in the same manner as in Reference example 10 to give the compounds as shown in the following Table 3.

TABLE 3

(structure II: cyclodextrin with OR¹ substituent, provided that 7 constitutional units are forming a cyclic ring in an arbitrary order through linkage between the 1-position and the 4-position)

| Reference example No. | Compound (II) R¹ | m | Form | Yield (%) | m.p. (°C.) |
|---|---|---|---|---|---|
| 11 | —CH₂—(phenyl) | 7 | Colorless needle | 96 | 150~153 |
| 12 | —CH₂—(phenyl) | 3 | Colorless powder | 70 | 262~264 (decomposed) |
| 13 | —CH₃ | 7 | Colorless powder | 60 | 250~255 (decomposed) |
| 14 | —CH₂—(phenyl)—CH₃ | 7 | Colorless powder | 48 | 80~100 |
| 15 | —CH₂—(phenyl)—F | 7 | Colorless powder | 57 | 180~190 |
| 16 | —CH₂—(phenyl)—Cl (meta) | 7 | Colorless powder | 51 | 215~225 (decomposed) |
| 17 | —CH₂CH=CH₂ | 7 | Colorless powder | 92 | 200~205 (decomposed) |
| 18 | —CH₂CH=CHC₂H₅ | 7 | Colorless powder | 78 | 145~150 (decomposed) |
| 19 | -n-C₈H₁₇ | 1 | Colorless needle | 51 | 280° C. or higher |

Reference Example 20

In 20 ml of methanol was dissolved 425 mg of heptakis(2-O-allyl)-β-cyclodextrin, and 400 mg of a 10% palladium-carbon catalyst was added to the resulting mixture. The mixture was shaken under hydrogen atmosphere at 3 kg/cm² at room temperature for 18 hours. The catalyst was removed by filtration, and the filtrate was evaporated to dryness under reduced pressure to give 420 mg of heptakis(2-O-n-propyl)-β-cyclodextrin as a colorless powder.
m.p.: 233° to 238° C. (decomposed)

Reference Example 21

In the same manner as in Reference example 20, heptakis(2-O-2-pentenyl)-β-cyclodextrin was treated to give heptakis(2-O-n-pentyl)-β-cyclodextrin as a colorless powder.
m.p.: 200° to 205° C. (decomposed)

Test Example 1
HIV Proliferation Inhibitory Activity

Principle

It is known that when MT-4 cells which are sustaining infectious cell lines of human T-cell Leukemia virus I type (HTLV-I) are infected with HIV, HIV proliferates rapidly and the MT-4 cells are killed in 5 to 6 days due to the cellular damage. Therefore, HIV proliferation inhibitory activity of a sample can be evaluated by examining the number of viable cells of the MT-4 cells infected with HIV.

Procedure

MT-4 cells were infected with HIV (a culture supernatant of TALL-1/LAV-1) at 37° C. for one hour so that TCID₅₀ (median tissue culture infectious dose)/cell might be 0.001, followed by washing with the medium. The infected MT-4 cells were then suspended at a concentration of 1×10⁵ cell/ml in RPMI-1640 media (containing 10% of FCS (fetal calf serum)) containing samples of various concentrations, respectively. Each of the thus obtained cell suspension was introduced in a flat bottom culture plate in an amount of 200 μl/well and was incubated at 37° C. in the presence of 5% carbon dioxide for 5 days. After incubation, the number of viable cells in the cell suspension was counted by the Tripan-Blue Staining Method. The HIV proliferation inhibitory activity of a sample was evaluated in terms of the concentration of the sample which suppresses by 100% the infectiousness and the cell modification activity of HIV in MT-4 cells.

Results

The results are shown in the following Table 4.

TABLE 4

| Test compound | HIV proliferation inhibitory activity, 100% inhibition concentration (μg/ml) |
|---|---|
| Polysulfate compound prepared in Example 1 (Sodium salt) | 0.98 |
| Polysulfate compound prepared in Example 2 (Potassium salt) | 1.95 |
| Polysulfate compound prepared in Example 3 (Potassium salt) | 1.95 |
| Polysulfate compound prepared in Example 6 (Sodium salt) | 3.9 |

Test Example 2

HIV proliferation inhibitory activity (in the presence of Human Serum)

Procedure

MT-4 cells were infected with HIV (a culture supernatant of TALL-1/LAV-1) at 37° C. for one hour so that $TCID_{50}$ (median tissue culture infectious dose)/cell might be 0.001, followed by washing with the medium. The infected MT-4 cells were then suspended at a concentration of $1 \times 10^5$ cell/ml in RPMI-1640 media (containing 50% of HS (Human Serum)) containing samples of various concentrations, respectively. Each of the thus obtained cell suspension was introduced in a flat bottom culture plate in an amount of 1 ml/well and was incubated at 37° C. in the presence of 5% carbon dioxide for 5 days. After incubation, the number of viable cells in the cell suspension was counted by the Tripan-Blue Staining Method. The HIV proliferation inhibitory activity of a sample was evaluated in terms of the concentration of the sample which suppresses by 50% the infectiousness and the cell modification activity of HIV in MT-4 cells.

Results

The results are shown in the following Table 5.

TABLE 5

| Test compound | HIV proliferation inhibitory activity, 50% inhibition concentration (μg/ml) |
|---|---|
| Polysulfate compound prepared in Example 1 (Sodium salt) | 0.87 |

Test Example 3

Giant cell formation inhibitory activity

Principle

When Molt-4 cell is co-cultured with Molt-4/HIV cell which is persistant-infected with HIV (HTLV-III B), a giant cell is formed within 1 to 2 days. This phenomenon is caused by linkage between CD4 receptor on the surface of Molt-4 cell and HIV envelope protein gp120 produced on the surface of Molt-4/HIV cell. Therefore, inhibitory activity on linkage between specimen HIV and CD4 molecule (adsorption of HIV to lymphocyte) can be evaluated by the presence of giant cell formation.

Procedure

To each well of flat-bottomed culture plate were added a serially diluted solution of test compound (various concentrations), healthy human serum (50%) and a cell suspension of a mixture of Molt-4 cell and Molt-4/HTLV-III B cell (1:1) ($5 \times 10^5$ cells/ml, 1 ml), followed by culture. After 22 hours, the number of viable cells was counted by the trypan blue exclusion method, and $IC_{50}$ (50% inhibitory concentration that reduced the number of giant cells by 50% was calculated.

Results

The results are shown in the following Table 6.

TABLE 6

| Test compound | Inhibitory activity on HIV-induced giant cell formation, 50% inhibition concentration (μg/ml) |
|---|---|
| Polysulfate compound prepared in Example 1 (Sodium salt) | 0.81 |

The polysulfate compound of the present invention is characterized by excellent antiretrovirus activity, particularly excellent HIV proliferation inhibitory activity and giant cell formation inhibitory activity as described above and further by low toxicity, proving high safety as pharmaceuticals.

We claim:

1. A polysulfate of a β-cyclodextrin in which at least one of 7 D-glucose units constituting the β-cyclodextrin is a unit represented by the formula (I-a):

$$\left[ \begin{array}{c} \text{OH} \\ \text{O} \\ \text{OH} \\ \text{OR}^1 \end{array} \right] \quad \text{(I-a)}$$

wherein $R^1$ is an alkyl group having 1 to 8 carbon atoms, a lower alkyl group substitued by a phenyl group or a lower alkenyl group, or a salt thereof.

2. The compound according to claim 1, wherein $R^1$ is a phenyl-substituted lower alkyl group.

3. The compound according to claim 1, wherein $R^1$ is benzyl group.

4. The compound according to claim 3, wherein said polysulfate has 9 to 18 sulfate groups.

5. Heptakis(2-O-benzyl)-β-cyclodextrin polysulfate or a salt thereof.

6. The compound according to claim 1, wherein said polysulfate has 8 to 20 sulfate groups.

7. A pharmaceutical composition which comprises a therapeutically effective amount of the compound claimed in claim 1 and a pharmaceutically acceptable carrier therefor.

* * * * *